US005734035A

United States Patent [19]

Sharp et al.

[11] Patent Number: 5,734,035
[45] Date of Patent: Mar. 31, 1998

[54] NEMATODE VACCINE

[75] Inventors: Phillip John Sharp, Glebe; Barry Maxwell Wagland, Carlingford, both of Australia

[73] Assignees: Biotech Australia Pty Limited, Roseville; Commonwealth Scientific and Industrial Research Organisation, Campbell, both of Australia

[21] Appl. No.: 461,005

[22] Filed: Jun. 5, 1995

Related U.S. Application Data

[62] Division of Ser. No. 930,685, Oct. 6, 1992.

[30] Foreign Application Priority Data

Feb. 6, 1991 [AU] Australia ............... PK 4487

[51] Int. Cl.$^6$ ............... C12N 15/11; C12N 15/00; A61K 39/00; C07K 14/00
[52] U.S. Cl. ............... 536/23.1; 536/23.5; 424/93.1; 424/184.1; 424/265.1; 530/350; 435/69.1; 435/240.2; 435/252.3; 435/254.11; 435/254.2; 435/320.1
[58] Field of Search ............... 424/184.1, 265.1, 424/93.1; 536/23.1, 23.5; 435/69.1, 240.2, 252.3, 254.11, 254.2, 320.1; 530/350

[56] References Cited

U.S. PATENT DOCUMENTS 4,879,213  11/1989  Fox et al.

FOREIGN PATENT DOCUMENTS

| 49035/90 | 10/1990 | Australia. |
| 89/00163 | 1/1989 | WIPO. |
| 90/03433 | 4/1990 | WIPO. |
| 90/11086 | 10/1990 | WIPO. |

OTHER PUBLICATIONS

Friedlander et al., "Immunological Aspects of Murine Infection with the Rat Nematode *Strongyloides ratti* Sandground, 1925," Z Parasitenkd. 72: 493–509 (1986).

Kennedy et al., "Stage–Specific Secreted Antigens of the Parasitic Larval Stages of the Nemadote Ascaris," Immunology. 58: 515–522 (1986).

O'Donnell, "Attempts to Probe the Antigens and Protective Immunogens of Trichostrongylus, etc . . . ", International Journal of Parasitology, vol. 15, No. 2, pp. 129–136, 1985.

Van Regenmortel, "Structural and Functional Approaches to the Study of Protein Antigenicity", Immunology Today, vol. 10, No. 8, 1989, pp. 266–272.

P. Stern, "Predicting Antigenic Sites on Proteins", TIBTECH, vol. 9, May 1991, pp. 163–168.

Ibrahim et al., "Antigen Shedding from the Surface of the Infective Stage Larvae of *Dirofilaria immitis*", Parasitology, vol. 99, 1989, pp. 89–97.

Geysen et al., "Cognitive Features of Continuous Antigenic Determinants", Journal of Molecular Recognition, vol. 1, No. 1, 1988, pp. 32–41.

Lehninger in *Biochemistry* (1975) 2nd Edition, Worth Publishers NY, NY. p. 63.

Burgess et al (1990) J. Cell Biol. vol. 111, 2129–2138.

Lazar et al (1988) Mol. and Cell. Biol. vol. 8 (3), 1247–1252.

*Primary Examiner*—Paula K. Hutzell
*Assistant Examiner*—Khalid Masood
*Attorney, Agent, or Firm*—Foley & Lardner

[57] ABSTRACT

Disclosed is a substantially purified antigen derived from a first parasitic nematode species which, when administered to a host animal, is capable of protecting the host animal from infestation by a second parasitic nematode species, wherein the first and second parasitic nematode species may be the same or different, and the antigen has an apparent molecular weight of 40 kD as determined by SDS-PAGE under reducing conditions.

18 Claims, 1 Drawing Sheet

FIG. 1

```
                10          19           28          37          46          55
        CGGCCGC TTC GTA CTA ACG ATT CTG GTG GCT TCG GCA TCT TCG GCA ACG AAA AAT
                Phe Val Leu Thr Ile Leu Val Ala Ser Ala Ser Ser Ala Thr Lys Asn 64          73           82          91         100         109
        TGC GAG ACT TCA GAA CCT CCT CCA GAT GAA TTC CAT TGT CAA ATC AAC GGC ACC
        Cys Glu Thr Ser Glu Pro Pro Pro Asp Glu Phe His Cys Gln Ile Asn Gly Thr 118         127          136         145         154         163
        ACC ATG ACC CCT GAA AAA CGA AAG CTT TCC GTA ATG CTG GGA AAT GCT TAT CGT
        Thr Met Thr Pro Glu Lys Arg Lys Leu Ser Val Met Leu Gly Asn Ala Tyr Arg 172         181          190         199         208         217
        ACA CTA GCA ACA TCT GGA GTA TTT GGG TAT CCA CCA AGC CAG AAC ATG TAT CAA
        Thr Leu Ala Thr Ser Gly Val Phe Gly Tyr Pro Pro Ser Gln Asn Met Tyr Gln 226         235          244         253         262         271
        TTG AAC TAC TCC TGC TTG GCT GAG AAA TAT GCA ATG GTA CTC TGC AAC CAA CAA
        Leu Asn Tyr Ser Cys Leu Ala Glu Lys Tyr Ala Met Val Leu Cys Asn Gln Gln 280         289          298         307         316         325
        GCA CCA CTC AAA CCT GTA GGG TAC AAT CTG TCT TCT ATC CCA TTA GCA GCA GCA
        Ala Pro Leu Lys Pro Val Gly Tyr Asn Leu Ser Ser Ile Pro Leu Ala Ala Ala 334         343          352         361         370         379
        TTC GAA TTG TGG TGG GGC AAT CAC GAC TTT GGT GCT TTT ATC AAT GAA ACT GGA
        Phe Glu Leu Trp Trp Gly Asn His Asp Phe Gly Ala Phe Ile Asn Glu Thr Gly 388         397          406         415         424         433
        GTC TAC AGC CCT AAC TTT GAT TAT ACC GTG TTC ACA CAA ATG GTT TCG GGT TAC
        Val Tyr Ser Pro Asn Phe Asp Tyr Thr Val Phe Thr Gln Met Val Ser Gly Tyr 442         451          460         469         478         487
        GCC GTC AGT ATA GGG TGC ACC GAT ACG TGC TAT GGC AAA CAA CAG GCG TAT TGC
        Ala Val Ser Ile Gly Cys Thr Asp Thr Cys Tyr Gly Lys Gln Gln Ala Tyr Cys 496         505          514         523         532         541
        GCA TTC GAA GTT TGC ACA GCC ATG ACT TAC TTC GGC ATG ATC TAC GAA GCA GGA
        Ala Phe Glu Val Cys Thr Ala Met Thr Tyr Phe Gly Met Ile Tyr Glu Ala Gly 550         559          568         577         586         595
        TCT GGT CCA TGT ATG GCC GAT AGT GAC TGC ACC ACG TAT CCT GGG TCC ACG TGC
        Ser Gly Pro Cys Met Ala Asp Ser Asp Cys Thr Thr Tyr Pro Gly Ser Thr Cys 604         613          622         631         640         649
        AAT ATG GCA AAT GGA TTG TGT GTC AAG CAA CCA AAC ACT CCT CTC TGC CCG AAA
        Asn Met Ala Asn Gly Leu Cys Val Lys Gln Pro Asn Thr Pro Leu Cys Pro Lys 658         667          677         687         697         707   717
        AAG ACA AAC TTA TAT TAA CGGCAACAAC AATAACAATA ATCCCATCCC ATATACAGCC TTACAACTCC
        Lys Thr Asn Leu Tyr

GTCTAATGCT GATAATCACA TATTAATTAC AATGGGAAGG AGAATAAATT GCGGCCGCC 776
```

NEMATODE VACCINE

This application is a divisional of application Ser. No. 07/930,685, filed on Oct. 6, 1992.

TECHNICAL FIELD

The invention relates to antigens which confer protective immunity against infection by parasitic nematodes.

The invention also relates to vaccines conferring protective immunity against infection by parasitic nematodes, and to antibodies conferring passive immunity to infection by parasitic nematodes.

BACKGROUND ART

Nematodes (nema-thread; oides-resembling), which are unsegmented roundworms with elongated, fusiform, or sac-like bodies covered with cuticle, are virtually ubiquitous in nature, inhabiting soil, water and plants, and are importantly involved in a wide range of animal and plant parasitic diseases.

The roundworm parasites of mammals belong to the phylum Nemathelminthes. The roundworms include the hookwork (e.g. *Necator americanus* and *Ancylostoma duodenale*), roundworm (eg the common roundworm *Ascaris lumbricoides*), whipworm (e.g. *Trichuris trichiura*), and the pinworm or threadworm (e.g. *Enterobius vermicularus*), as well as *Strongyloides stercoralis*, *Trichinella spiralis* (infection in man and pigs) and the filarial worm *Wuchereria bancrofti*. Other important roundworm parasites include *Ancylostoma caninum* (infections of man), *Strongylus vulgaris* (infections of horses), *Haemonchus contortus*, *Trichostrongylus colubriformis*, *Ostertagia circumcincta* (infections of sheep and goats), *Ostertagia ostertagi*, *Haemonchus placei* (infections of cattle), *Ascaris suum* (infections in pigs), *Toxascaris leonia* or *Uncinaria stenocephala* (infections of dogs), *Toxocara* species (circulatory infections of man) and *Dirofilaria immitis* (circulatory infections of cats and dogs).

Even when symptom-free, parasitic worm, infections are harmful to the host animal for a number of reasons; e.g. they deprive the host of food, injure organs or obstruct ducts, may elaborate substances toxic to the host, and provide a port of entry for other organisms. In other cases, the host may be a species raised for food and the parasite may be transmitted upon eating to infect the ingesting animal. It is highly desirable to eliminate such parasites as soon as they have been discovered.

More commonly, such infections are not symptom free. Helminth infections of mammals, particularly by parasitic nematodes are a source of great economic loss, especially of livestock and pets, e.g. sheep, cattle, horses, pigs, goats, dogs, cats and birds, especially poultry. These animals must be regularly treated with anthelminthic chemicals in order to keep such infections under control or else the disease may result in anaemia, diarrhoea, dehydration, loss of appetite and even death.

The only currently available means for controlling helminth infections is with the use of anthelminthic chemicals, but these are only effective against resident worms present at the time of treatment. Therefore, treatment must be frequent or continuous since the animals are constantly exposed to infection; e.g. anthelminthic treatment with diethylcarbamazine is required every day or every other day most of the year to control *Dirofilaria immitis* or the dog heartworm. This is an expensive and labour intensive procedure. Due to the widespread use of anthelminthic chemicals, the worms may develop resistance and so new and more potent classes of chemicals must be developed. An alternative approach is clearly desirable.

The development of a vaccine against parasitic nematodes would overcome many of the drawbacks inherent in chemical treatment for the prevention and curing of helminthic infections. The protection would certainly last longer, only the vaccinated animals would be affected, and the problems of toxicity and persistence of residues would be minimized or avoided.

Accordingly, there have been reported attempts to develop such vaccines using parasitic nematodes; unfortunately, they have met with limited success and factors such as material availability and vaccine stability have precluded their large scale use.

These previous attempts are discussed in International Patent Application No. PCT/AU88/00239 (WO 89/00163) and PCT/AU89/00416 (WO 90/03433).

Recent advances in biotechnology and in particular recombinant DNA technology, realistically offer the opportunity to produce commercially-viable vaccines against a range of economically-important parasites of man and domestic animals. This approach would overcome many of the problems proposed to account for the lack of efficacy of killed vaccines using crude parasite preparations. For example, the vaccines produced by recombinant DNA techniques would not contain immunosuppressants or immunomodulators which may be found in crude extracts of parasitic nematode species. But it is necessary to first identify the antigens. Once identified and characterised, recombinant DNA technology could be used to construct microorganisms which synthesize those proteins or portions of the proteins containing protective epitopes and use the products synthesized by the recombinant organism in vaccines to protect animals from infection with the parasites.

In PCT/AU88/00239 it has been demonstrated that a recombinant DNA derived antigen shown to be nematode tropomyosin, gave 50% protection in sheep against *Haemonchus contortus* challenge. In PCT/AU89/00416 excretory/secretory antigens from adult *Trichostrongylus colubriformis* have been shown to give protection to vaccinated guinea pigs. For reasons which will become clear later in this specification, these antigens are different from the antigen identified in the current specification: the current novel antigen being found in the excretory/secretory fluids of third stage larval nematodes following exsheathment and incubation in vitro.

DESCRIPTION OF THE INVENTION

Definitions

The term "adjuvant" as used throughout the specification refers to an agent used to enhance the immune response of the immunised host to the immunising composition.

The term "parenteral" as used herein includes subcutaneous injections, intraperitoneal or intramuscular injection, or infusion techniques.

The term "homologue" refers to proteins or to DNA sequences coding for those proteins which are related in structure to a first protein or DNA sequence to such an extent that it is clear that the proteins are related in function. In the context of this invention, DNA from *H. contortus* which codes for the protective antigen of the invention can be used in DNA hybridisation experiments to identify specific DNA sequences in other species of parasitic nematodes. These related DNA segments should code for antigens in those other species of parasitic nematodes which are also related in amino acid sequence to the protective antigen isolated from *H. contortus*. It is contended that the related proteins will act as effective immunogens to protect animals from parasitism by the other species of parasites. These related DNA sequences are referred to as homologous genes and the related proteins are referred to as homologous antigens. The homology is predicted to be at least 70% over 20 amino acids at the amino acid sequence level and at least 50% over 60 nucleotides at the DNA level. Also, in the context of the present invention, there is evidence that the protective antigen is a member of a "gene family" wherein the encoding polynucleotide and the gene product share an homology of the order of 50% over 60 nucleotides or 70% over 20 amino acids respectively, with the encoding gene and protective antigen of this invention. These related genes and gene products are also homologues of this invention. Homologues of the invention may also be generated in vitro as hereinafter described.

The term "derived" in the context of the antigens of the invention, as used herein, is intended to encompass antigens obtained by isolation from a parasitic nematode life stage expressing the antigen, as well as antigens obtained by manipulation of and expression from nucleotide sequences encoding the antigen prepared from a parasitic nematode life stage, including genomic DNA, mRNA, cDNA synthesized from mRNA and synthetic nucleotides prepared to have sequences corresponding to the antigen encoding sequences.

It is also intended to encompass synthetic peptide antigens prepared on the basis of the known amino acid sequences of the antigens as expressed by nematodes or cell lines expressing recombinant forms of the antigens.

Disclosure

It is preferable, if possible, to identify "novel" or "concealed" antigens i.e. components of the parasite which can act as effective and protective immunogens but which are not involved in naturally acquired immunity. To identify those components it is necessary to vaccinate the host with extracts from the parasite, identify fractions which give some protection, subfractionate the protective components using protein chemistry techniques, vaccinate animals with those subfractions and identify those subfractions which protect and continue with that process until a pure parasite component is used to vaccinate and protect the animal.

As much as possible, the natural host should be used in such experiments. As laboratory model animals are not the natural host for the parasite they are likely to be able to reject the parasite by mechanisms of which the natural host is incapable. Thus it is possible that antigens which protect laboratory animals against particular parasites may not be effective in the natural host of the parasite. This will be more likely to be the case in situations where the natural host develops immunity to the parasite very slowly.

The antigens characterized in the current work are derived from *Haemonchus contortus* but it is recognised that similar or related antigens, "homologues", could be identified from other species of parasitic nematode known to infect man or domestic animals and that these related antigens, would provide effective vaccines against parasitism by species of nematode. Species of parasites and hosts they may infect include for example:

*Trinchinella spiralis* or *Ancylostoma caninum* infections of man, *Strongylus vulgaris* infections of horses, *Trichostrongylus colubriformis* infections of sheep, *Haemonchus contortus* infections of goats, *Ostertagia ostertagi* infections of cattle, *Ascaris suum* or *Trichinella spiralis* infections of pigs, *Toxascaris leonina* or *Uncinaria stenocephala* infections of cats and *Ancylostoma caninum* or *Trichuris vulpis* infections of dogs as well as infections of the circulatory system of man by larvae of Toxocara spp and of the circulatory system of dogs by *Dirofilaria immitis* as well as infections of the circulatory system, urogenital system, respiratory system, skin and subcutaneous tissue of these and other species of animal. It should be noted that this list is by no means complete.

The present inventors have studied in detail the products released from exsheathed third stage larvae of *H. contortus* upon incubation in culture media. Those components which are capable of giving protection following vaccination of target animals have been purified and characterised at the molecular level.

The present inventors have found that protective immunity against infection by parasitic nematodes can be induced by immunization.

According to a first embodiment of the present invention there is provided a substantially purified antigen derived from a first parasitic nematode species which when administered to a host animal is capable of protecting the host animal from infestation by a second parasitic nematode species wherein the first and second parasitic nematode species may be the same or different, and the antigen has an apparent molecular weight of 40 kD as determined by SDS-PAGE under reducing conditions.

Typically, the purity is greater than 90%. This level of purity is demonstrated with respect to the cleanliness of the preparations used in amino acid sequencing.

Typically the first and second nematode species are selected from species of the genera Trichinella, Ancylostoma, Strongylus, Trichostrongylus, Haemonchus, Ostertagia, Ascaris, Toxascaris, Uncinaria, Trichuris, Dictycaulus, Dirofilaria, Toxocara, Necator, Enterobius, Strongyloides and Wuchereria, especially the genera Trichostrongylus and Haemonchus. Examples of such species include *Trichinella spiralis, Ancylostoma caninum, Strongylus vulgaris, Trichostrongylus colubriformis, Haemonchus contortus, Ostertagia ostertagi, Ascaris suum, Dictycaulus viviparus, Toxascaris leonina, Uncinaria stenocephala, Trichuris vulpis, Dirofilaria immitis,* the larvae of Toxocara species, *Necator americanus, Ancylostoma duodenale, Ascaris lumbricoides, Trichuris trichiura, Enterobius vermicularus, Strongyloides stercoralis* and *Wuchereria bancrofti,* particularly *Trichostrongylus colubriformis* and *Haemonchus contortus.*

According to a second embodiment of the present invention there is provided a homologue of an antigen of the first embodiment wherein the homologue when administered to a host animal is capable of protecting the host from infection by a parasitic nematode species. Typically the homologue is at least 70% homologous to the amino acid sequence of an antigen of the invention over 20 amino acids.

According to a third embodiment of the present invention, there is provided a polynucleotide molecule encoding an antigen or homologue of the invention.

Preferably the polynucleotide molecule is a DNA molecule. DNA molecules in accordance with the present invention include cDNA molecules.

According to a fourth embodiment of the present invention there is provided a recombinant DNA molecule which comprises a DNA molecule of the third embodiment and vector DNA.

Typically the vector DNA is selected from plasmid, viral and cosmid DNA.

Preferred vectors in accordance with the present invention include lambda gt 11, pUR 290, pUR 291, pUR 292, pUK 270, pUC 8, pUC 9, pZipNeo, an SV 40 based vector, lambda gt 10, an EMBL vector, pBR 327, pBR 329 or pBR 329 containing a par locus, baculovirus or vaccinia virus.

According to a fifth embodiment of the present invention there is provided a transformed host transformed with at least one recombinant DNA molecule of the fourth embodiment.

Typically, the host is selected from bacteria, yeasts, other fungi, insect, plant and mammalian cell lines.

Preferred hosts include *E. coli* K 12 derivatives.

According to a sixth embodiment of the present invention there is provided an expression product of a transformed host of the fifth embodiment which expression product comprises an antigen or a homologue of the invention.

The expression product may be a fusion product.

According to a seventh embodiment of the present invention there is provided a synthetic polypeptide corresponding to all or part of an antigen, homologue or expression product of the invention which synthetic polypeptide when administered to a host animal is capable of inducing protective immunity against infestation of the host animal by a parasitic nematode.

The synthetic polypeptides of the invention are prepared by standard techniques of peptide synthesis based on known sequences of antigens, homologues and expression products of the invention.

According to an eighth embodiment of the present invention there is provided a vaccine comprising at least one antigen, homologue, expression product and/or synthetic polypeptide of the invention together with a pharmaceutically and/or veterinarally acceptable, carrier, diluent, excipient and/or adjuvant. The vaccines of the invention could alternatively comprise at least one anti-idiotypic antibody capable of protecting a host from infection by a parasitic nematode by mimicking an antigen, homologue, expression product and/or synthetic polypeptide of the invention. A pharmaceutically and/or veterinarally acceptable carrier, diluent, excipient and/or adjuvant may be added to the active component.

As a further alternative, the vaccine may be a whole cell vaccine comprising a transformed host of the fifth embodiment together with a pharmaceutically and/or veterinarally acceptable carrier, diluent, excipient and/or adjuvant. The cells may be live or killed. The transformed cells include those capable of expressing the expression product for mucosal presentation to a host to be vaccinated, such as, as a cell surface fusion product.

Typically, the vaccines of the invention induce in a vaccinated host, protective immunity against infection by parasitic nematodes such as species of the genera Trichinella, Ancylostoma, Strongylus, Trichostrongylus, Haemonchus, Ostertagia, Ascaris, Toxascaris, Uncinaria, Trichuris, Dictycaulus, Dirofilaria, Toxocara, Necator, Enterobius, Strongyloides and Wuchereria, especially the genera Trichostrongylus and Haemonchus. Examples of such species include *Trichinella spiralis*, or *Ancylostoma caninum* in man, *Strongylus vulgaris* in horses, *Trichostrongylus colubriformis* in sheep and goats, *Haemonchus contortus* in sheep and goats, *Ostertagia ostertagi* in cattle, *Ascaris suum*, or *Trichinella spiralis* in pigs, *Toxascaris leonina* or *Uncinaria stenocephala* in cats, *Ancylostoma caninum* or *Trichuris vulpis* in dogs, *Dirofilaria immitis* in dogs, or the larvae of Toxocara spp. in man, or infection by *Necator americanus, Dictycaulus viviparus, Ancylostoma duodenale, Ascaris lumbricoides, Trichuris trichiura,* *Enterobius vermicularus, Strongyloides stercoralis* or *Wuchereria bancrofti*, particularly *Trichostronglyus colubriformis* or *Haemonchus contortus*.

According to a ninth embodiment of the present invention there is provided an antibody raised against an antigen, homologue, expression product, synthetic polypeptide or vaccine of the present invention.

The antibodies of the invention include polyclonal and monoclonal antibodies and are prepared in accordance with standard techniques of antibody preparation.

According to a tenth embodiment of the present invention there is provided an antibody composition comprising at least one antibody of the ninth embodiment together with a pharmaceutically and/or veterinarally acceptable carrier, diluent and/or excipient.

According to an eleventh embodiment of the present invention there is provided a diagnostic kit comprising a sample of an antigen, homologue, expression product or synthetic polypeptide of the present invention and/or an antibody of the present invention.

According to a twelfth embodiment of the present invention, there is provided a process for the biosynthesis of an expression product of the sixth embodiment which process comprises providing a transformed host of the fifth embodiment, culturing the host under suitable conditions to obtain expression of the expression product and collecting the expression product from the transformed host.

According to a thirteenth embodiment of the present invention there is provided a method of protecting a host against infestation by a parasitic nematode species which method comprises vaccinating the host with at least one antigen, homologue, expression product, synthetic polypeptide and/or vaccine of the invention.

According to a fourteenth embodiment of the present invention there is provided a process for preparing a recombinant DNA molecule of the fourth embodiment which process comprises inserting a DNA molecule of the third embodiment into vector DNA.

According to a fifteenth embodiment of the present invention there is provided a process for preparing a transformed host of the fifth embodiment which process comprises making a host competent for transformation to provide a competent host and transforming the competent host with a recombinant DNA molecule of the fourth embodiment.

According to a sixteenth embodiment of the present invention there is provided a process for preparing an antibody of the ninth embodiment which process comprises immunizing an inmunoresponsive host with at least one antigen, homologue, expression product, synthetic polypeptide and/or vaccine of the invention.

According to a seventeenth embodiment of the present invention there is provided a process for preparing a vaccine of the eighth embodiment which process comprises admixing an effective amount of at least one antigen, homologue, expression product synthetic polypeptide and/or transformed host and/or antiidiotype antibody of the invention with a pharmaceutically and/or veterinarally acceptable carrier, diluent, excipient and/or adjuvant.

According to an eighteenth embodiment of the present invention there is provided a process for preparing an antibody composition of the tenth embodiment which process comprises admixing an effective amount of an antibody of the ninth embodiment with a pharmaceutically and/or veterinarally acceptable carrier, diluent and/or excipient.

According to a nineteenth embodiment of the present invention there is provided a method of passively vaccinating a host against a parasitic nematode species comprising administering an antibody of the ninth embodiment or an antibody composition of the tenth embodiment to the host.

It is recognised that variation in amino acid and nucleotide sequences can occur between different allelic forms of a particular protein and the gene(s) encoding the protein. Further once the sequence of a particular gene or protein is known a skilled addressee, using available techniques, would be able to manipulate those sequences in order to alter them from the specific sequences obtained to provide a gene or protein which still functions in the same way as the gene or protein to which it is related. These molecules are referred to hereinafter as "homologues" and are intended also to be encompassed by the present invention.

In this regard, a "homologue" is a polypeptide that retains the basic functional attribute namely, the protective activity of an antigen of the invention, and that is homologous to an antigen of the invention. For purposes of this description, "homology" between two sequences connotes a likeness short of identity indicative of a derivation of the first sequence from the second. In particular, a polypeptide is "homologous" to an antigen of the invention if a comparison of amino-acid sequences between the polypeptide and the antigen, reveals an identity of greater than about 70% over 20 amino acids. Such a sequence comparison can be performed via known algorithms, such as the one described by Lipman and Pearson, *Science* 227: 1435 (1985), which are readily implemented by computer.

Homologues can be produced, in accordance with the present invention, by conventional site-directed mutagenesis, which is one avenue for routinely identifying residues of the molecule that can be modified without rendering the resulting polypeptide biologically inactive. Oligonucleotide-directed mutagenesis, comprising [i] synthesis of an oligonucleotide with a sequence that contains the desired nucleotide substitution (mutation), [ii] hybridizing the oligonucleotide to a template comprising a structural sequence coding for an antigen of the invention and [iii] using T4 DNA polymerase to extend the oligonucleotide as a primer, is preferred because of its ready utility in determining the effects of particular changes to the antigen structural sequence. Its relative expense may militate in favour of an alternative, known direct-mutagenesis method.

Also exemplary of antigen homologues within the present invention are molecules that correspond to a portion of the antigen, or that comprise a portion of the antigen without being coincident with the natural molecule, and that display the protective activity of an antigen of the invention.

Other homologues of the present invention are fragments of the antigen that retain protective activity. Likewise within the present invention would be synthetic polypeptides that (i) correspond to a portion of the antigen amino-acid sequence and (ii) retain an activity characteristic of the antigen. Such synthetic polypeptides would preferably be between 6 and 30 amino residues in length.

Whether a synthetic polypeptide meeting criterion (i) also satisfies criterion (ii) can be routinely determined by assaying for protective activity, in an appropriate host.

The invention provides a method of protecting a mammalian host against infestation by a parasitic nematode which method comprises vaccinating a mammalian host with at least one antigen, homologue, expression product, synthetic polypeptide and/or a vaccine of the present invention. Vaccines of the present invention can be formulated using standard techniques.

The amount of antigen, homologue, expression product and/or synthetic polypeptide that may be combined with carrier to produce a single dosage form will vary depending upon the infestation being prevented, the host to be treated and the particular mode of administration.

It will be understood, also, that the specific dose level for any particular host will depend upon a variety of factors including the activity of the specific antigen, homologue, expression product and/or synthetic polypeptide employed, the age, body weight, general health, sex, diet of the patient, time of administration, route of administration, rate of excretion, drug combination, etc.

The vaccines of the present invention may be administered parenterally or potentially via mucosal routes in dosage unit formulations containing conventional, non-toxic, pharmaceutically and/or veterinarally acceptable carriers, diluents, adjuvants and/or excipients as desired.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

At present alum is the only registered adjuvant for human use, however, experimental work is being conducted on other adjuvants for human use and it is anticipated that these other adjuvants would be suitable for use in preparing compositions for human vaccination in accordance with this invention.

Suitable adjuvants for the vaccination of animals include but are not limited to oil emulsions such a Freund's complete or incomplete adjuvant (not suitable for livestock use), Marcol 52: Montanide 888 (Marcol is a Trademark of Esso, Montanide is a Trademark of SEPPIC, Paris), squalane or squalene, Adjuvant 65 (containing peanut oil, mannide monooleate and aluminium monostearate), mineral gels such as aluminium hydroxide, aluminium phosphate, calcium phosphate and alum, surfactants such a hexadecylamine, octadecylamine, lysolecithin, dimethyldioctadecylammonium bromide, N,N-dioctadecyl-N',N'-bis(2-hydroxyethyl) propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. The antigens, homologues, expression products and/or synthetic polypeptides of the present invention can also be administered following incorporation into liposomes or other micro-carriers, or after conjugation to polysaccharides, proteins or polymers or in combination with Quil-A to form "Iscoms" (Immunostimulating complexes). Other adjuvants suitable for use in the present invention include conjugates comprising the antigen together with an integral membrane protein of prokaryotic origin, such as TraT. (See PCT/AU87/00107).

Routes of administration, dosages to be administered as well as frequency of injections are all factors which can be optimised using ordinary skill in the art. Typically, the initial vaccination is followed some weeks later by one or more "booster" vacinations, the net effect of which is the production of vigorous immune response both humoral and cellular.

BRIEF DESCRIPTION OF THE DRAWINGS

FIG. 1 (SEQ ID NOS. 12–13) shows the sequence of cDNA clone pBTA 983 which codes for the 40 kD antigen.

BEST METHOD OF CARRYING OUT THE INVENTION

The recombinant DNA molecules and transformed host cells of the invention are prepared using standard techniques of molecular biology.

Expression products of the invention are obtained by culturing transformed host cells of the invention under standard conditions as appropriate to the particular host cell and separating the expression product from the culture by standard techniques. The expression product may be used in impure form or may be purified by standard techniques as appropriate to the expression product being produced. Where appropriate, whole cells may be used in vaccines.

The synthetic polypeptides of the invention are prepared by standard techniques of chemical peptide synthesis from the known sequences of antigens, homologues or expression products of the invention.

The homologues, expression products, synthetic polypeptides, anti-idiotype antibodies and vaccines of the invention can readily be assayed by the methods described in the Examples to determine whether they maintain the protective effect of the antigens of the invention. Those molecules which retain protective activity fall within the scope of the present invention.

Recombinant DNA technology can be used to provide a large amount of the protective antigen or homologues described herein. The DNA segment coding for the protective antigen or the precursor for the protective antigen or homologue can be inserted into any of a number of recombinant plasmid systems to enable the molecule to be synthesised in large amounts. The recombinant systems include E. coli, yeast and baculovirus system and viruses such as vaccinia. The recombinant organisms can be grown in large volumes in fermenters and the recombinant antigens purified by standard methods—solubilisation in solutions containing urea and reducing agents such as DTT or mercaptoethanol, refolding in the presence of reagents such as reduced and oxidised glutathione, purification by ion exchange, filtration and/or gel permeation chromatography, terminally sterilised by filtration and adjuvanted in any of a number of adjuvants including oils.

The vaccines of the invention are prepared by mixing, preferably homogeneously mixing, at least one antigen, homologue, expression product, synthetic polypeptide and/or transformed host and/or antiidiotype antibody of the invention, with a pharmaceutically acceptable carrier, diluent, excipient and/or adjuvant using standard methods of pharmaceutical preparation.

The amount of antigen, homologue, expression product, synthetic polypeptide and/or transformed host and/or anti-idiotype antibody required to produce a single dosage form will vary depending upon the particular infection prevented, host to be treated and the particular mode of administration. The specific dose level for any particular host will depend upon a variety of factors including the activity of the antigen, homologue, expression product and/or synthetic polypeptide employed, the age, body weight, general health, sex, and diet of the patient, time of administration, route of administration, rate of excretion, drug combination etc.

The vaccine may be administered parenterally in unit dosage formulations containing conventional, non-toxic, pharmaceutically and/or veterinarally acceptable carriers, diluents, excipients and/or adjuvants as desired.

Antibodies are raised using standard vaccination regimes in appropriate hosts. The host is vaccinated with an antigen, homologue, expression product, synthetic polypeptide and/or vaccine of the invention.

Antiidiotypes are raised by vaccinating a suitable host with an antigen, expression product, homologue, synthetic polypeptide and/or vaccine of the invention and using the resulting antibodies to raise antibodies against the antigen binding region of the antibodies raised in the first vaccination.

The antibody composition is prepared by mixing, preferably homogeneously mixing, antibody with a pharmaceutically and/or veterinarally acceptable carrier, diluent, and/or excipient using standard methods of pharmaceutical preparation.

The amount of antibody required to produce a single dosage form will vary depending upon the infection to be treated, host to be treated and the particular mode of administration. The specific dose level for any particular host will depend upon a variety of factors including the activity of the antibody employed, the age, body weight, general health, sex, and diet of the patient, time of administration, route of administration, rate of excretion, drug combination, etc.

The antibody composition may be administered parenterally in unit dosage formulations containing conventional, non-toxic, pharmaceutically and/or veterinarally acceptable carriers, diluents, and/or excipients as desired to passively protect hosts against nematode infestation.

Diagnostic kits are prepared by formulating expression product, antibodies, antigen, synthetic polypeptide or homologue at appropriate concentration to the substance(s) to be detected with a pharmaceutically and/or veterinarally acceptable carrier, diluent and/or excipient. A positive control standard of a known concentration of the substance to be detected is prepared similarly. The negative standard comprises carrier, diluent and/or excipient alone.

The invention is further described with reference to the following examples, which are not limiting on the scope of the present invention.

EXAMPLE 1

Preparation of Culture Fluid from Infective *H. contortus* Larvae

Larvae were cultured from the faeces of sheep infected with *H. contortus* and stored at 10° C. for 2 weeks before use. At this time ca. $2 \times 10^7$ larvae which migrated through a 25 μm mesh sieve were collected and washed. Larvae were then exsheathed by suspension in 20 mM borate buffer and gassing with 40% $CO_2$-60%$N_2$ at 40° C. Exsheathing fluid was removed by washing over a Buchner funnel and larvae were Baermanized to remove sheaths. The worms were washed in GKN medium (GIBCO) containing penicillin (200 units/ml) and streptomycin (200 μg/ml) and incubated in the same medium during roller bottle culture (approximately 200,000 worms/ml.) for 72–144 hours at 37° C. The viability of the worms was monitored by visual inspection and routinely >95% were alive and 30–40% had developed to the fourth stage.

The larvae were removed by centrifugation and the supernatant was concentrated 10-fold by ultrafiltration using an Amicon YM-10 membrane. The retentate is referred to as "Culture fluid".

EXAMPLE 2

Vaccination of Guinea Pigs with Culture Fluid

Culture fluid was prepared from infective larvae as described in Example 1. This material was used to vaccinate guinea pigs intraperitoneally using the procedure described by O'Donnell et al. (1985). 21 days later the guinea pigs were infected with 1000 *H. contortus* L3 larvae (exsheathed) and slaughtered for worm counts 5 days post challenge. It can be seen (Table 1) that the culture fluid gave highly significant protection in each experiment (64–90% reduction in parasitism) with the exception of the 72–144 hours culture fluid in experiment #277. The 0–72 hours culture period was optimal and was, therefore, used in each subsequent experiment.

TABLE 1

Protection of Guinea Pigs with HcL3 Culture Fluid

| Expt No. | Group | Culture Period (hrs) | Injected (µg) | n | Worm Nos. | Protection (%) |
|---|---|---|---|---|---|---|
| 273 | Controls | — | — | 8 | 717 ± 276 | — |
|  | Vaccinates | 0–72 | 50 | 8 | 124 ± 78 | 83 |
| 277 | Controls | — | — | 8 | 849 ± 192 | — |
|  | Vaccinates | 0–72 | 50 | 8 | 303 ± 197 | 64 |
|  | Vaccinates | 72–144 | 50 | 5 | 806 ± 139 | 5 |
| 279 | Controls | — | — | 10 | 1037 ± 103 | — |
|  | Vaccinates | 0–48 | 50 | 5 | 244 ± 136 | 77 |
|  | Vaccinates | 48–120 | 50 | 5 | 129 ± 45 | 88 |
| 285 | Controls | — | — | 5 | 612 ± 264 | — |
|  | Vaccinates | 0–72 | 50 | 5 | 63 ± 37 | 90 |

Legend to Table 1

Vaccinates were injected intraperitoneally with the culture fluid. Animals were challenged with 1000 larvae 21 days later and killed for worm counts 5 days post challenge.

EXAMPLE 3

Fractionation of Culture Fluid

The culture fluid was concentrated 20-fold by ultrafiltration over an Amicon YM-30 membrane and the retentate dialysed against Tris-buffered saline (TBS; 20 mM Tris, 150 mM NaCl, pH 7.2). The concentrated culture fluid was incubated with lentil lectin Sepharose-4B (Pharmacia) (300 ul packed volume) that had been crosslinked with glutaraldehyde (Scher, et al 1989). The slurry was mixed overnight at 4° C. before the beads were removed by centrifugation and washed with 3×15 ml TBS. The specifically-bound glycoprotein was eluted by incubation of the beads in 0.2M methyl-D-manoside in TBS for 2 hrs at room temperature and is referred to as LL$^+$ (MM). More strongly bound material was eluted subsequently with 0.2% SDS/0.1M acetic acid and neutralized with 2M Tris pH8.8 and is referred to as LL$^+$ (SDS/HOAc). When analysed by SDS-PAGE with reducing conditions both LL$^+$ fractions contained a predominant band with an apparent molecular weight of approximately 40 kD.

EXAMPLE 4

Vaccination of Guinea Pigs with Lentil Lectin Fractionated Culture Fluid

The material prepared from culture fluid by lentil lectin absorption was used to vaccinate guinea pigs intraperitoneally. The LL$^+$ (MM) and LL$^+$ (SDS/acetic acid [HOAc]) fractions containing predominantly the 40 kD antigen gave a highly significant degree of protection against subsequent challenge of those guinea pigs with *H. contortus* (Table 2). It is thus clear that the 40 kD component is capable of eliciting a protective immune response following vaccination. The non-bound (LL$^-$) fraction was also protective, however, this may have been due to the presence of some 40 kD material that was not bound to the lentil lectin beads.

TABLE 2

Protection of Guinea Pigs with YM-30 concentrated Culture Fluid [Cf (YM-30)] and fractions derived from it by Lentil Lectin absorption

| Expt No. | Group | Antigen | Injected (µg) | n | Worm Nos. | Protection (%) |
|---|---|---|---|---|---|---|
| 301 | Controls | — | — | 5 | 311 ± 142 | — |
|  | Vaccinates | Cf(YM-30) | 250 | 5 | 49 ± 60 | 84 |
|  | Vaccinates | LL$^-$ | 200 | 5 | 96 ± 68 | 72 |
|  | Vaccinates | LL$^+$(MM) | 50 | 5 | 50 ± 48 | 85 |
| 318 | Controls | — | — | 6 | 468 ± 129 | — |
|  | Vaccinates | Cf | 140 | 5 | 136 ± 115 | 71 |
|  | Vaccinates | LL$^-$ | 100 | 5 | 82 ± 38 | 82 |
|  | Vaccinates | LL$^+$(MM) | 50 | 5 | 72 ± 66 | 85 |
|  | Vaccinates | LL$^+$ (SDS/HOAc) | 50 | 5 | 21 ± 10 | 96 |

Legend to Table 2

Vaccinates were injected intraperitoneally with the relevant antigen. Animals were challenged with 1000 larvae 21 days later and killed for worm counts 5 days post challenge.

EXAMPLE 5

Digestion of 40 kD Antigen with Endoproteinase lys-C, Separation of Peptides and Determination of the Amino Acid Sequence of Peptides Approximately 25 µg of the 40 kD antigen purified as described in Example 3 was mixed with 200 µl of 0.2M Tris-HCl buffer pH 8.5 containing 5 mM dithiothreitol and 8M urea, then incubated at 42° C. for 30 min. The solution was then cooled to room temperature and sodium iodoacetate added to a final concentration of 15 mM. After 35 minutes in the dark, cold methanol was added in a ratio 9:1 (methanol:sample v/v). The sample was stored at −20° C. overnight, centrifuged, the supernatant aspirated and the precipitate dried.

The precipitate was dissolved in 45 µl of 0.1M Tris-HCl buffer containing 2M urea, pH 8.5, then 4 µl of Endo Lys-C (100 µg/ml) was added. After 5 hrs at 37° C., another 4 µl of enzyme was added and the digestion was continued for a further 15 hours. The digest was acidified by the addition of trifluoroacetic acid to a final concentration of 1% and applied directly to a Vydac C-4 column in 0.1% trifluoroacetic acid. The peptides were eluted with a linear gradient from 5–60% v/v acetonitrile/water in 0.1% trifluoroacetic acid. If necessary, peptides were rechromatographed in the same solvent system using an Aquapore RP-300 C-8 cartridge. Peptides were collected and applied directly to an Applied Biosystems 470A amino acid sequencer. The following peptide sequences which were obtained are shown in Table 3.

TABLE 3

Amino Acid Sequences derived from 40 kD Antigens (SEQ ID NO:1) (K)¹ (Q)²P N T P L G P K
(SEQ ID NO:2) (K)¹ (L)²S L M G N A Y R T L A (D)² (X)⁵ (G)⁴ V F (X)⁵ Y (P)⁴ P
                    (V)³
(SEQ ID NO:3) (K)¹ (N)² (X)⁵ E T S E P P P (X)⁵ E (F)² (X)⁵ (X)⁵ Q I I (G)⁴ (G)⁴
                                                                (L)³
(SEQ ID NO:4) (K)¹ (X)⁵ (X)⁵ E T S (S)⁴ P P P (E)⁴ (X)⁵ F (F)⁴
                              (P)³    (D)³
(SEQ ID NO:5) (K)¹ (N)² (X)⁵ E T S E P P P D E F (X)⁵ (G)⁴ Q I (X)⁵ (G)⁴
(SEQ ID NO:6) (K)¹ (Y)² (A)⁴ M V L (G)⁴ N (Q)⁴ Q A P L (G)⁴
                                   (Y)³         (S)³

In addition, the undigested 40 kD antigen [LL⁺(MM)] was
sequenced to elucidate the amino terminal sequence (SEQ ID NO:7).
A   K   K   N Y E T S E       P P P D E F H (X)⁵ Q I X G T T M (X)⁵ P E K
(D)³ (T)³ (E)³                                  (K)³
(X)⁵ (X)⁵ L (X)⁵ V (X)⁵ (L)⁴ (G)⁴ (N)⁴ (A)⁴

NOTES:
The following assumptions were made in interpreting the peptide sequences. Numbers 1 to 5 refer to superscripts in the sequences listed above.
1. It was assumed that a lysine (K) preceded the first amino acid which was determined for each peptide based on the specifity of the Endo Lys—C.
2. This position contained a number of amino acids, however, the one listed is assigned on the basis of highest molar ratio. The uncertainty is denoted by brackets.
3. More than one amino acid was detected.
4. These amino acids were assumed to be correct, although they were detected at lower molar ratios than expected.
5. No amino acid could be confidently ascribed to positions shown as X.

EXAMPLE 6
Molecular Cloning of the 40 kD Gene
(a) Oligonucleotide synthesis From the amino acid sequences described in Example 5, any of a number of oligonucleotides could be designed that could be used to screen CDNA and genomic DNA libraries to identify the gene(s) encoding the 40 kD antigen. In addition, oligonucleotides could be designed for use in conjunction with oligo (dT) in the polymerase chain reaction (PCR) (Saiki et al.,1988) specifically to amplify the DNA encoding the 40 kD protein.

For example, the following multiply degenerate primers (A140/301, A140/302 and A140/303 SEQ ID NOS. 8, 9 and 10, respectively) were designed and synthesized on an Applied Biosystems Model 380A automated DNA synthesizer. Nucleotides additional to those necessary to encode the required amino acid sequence were included on the 5' ends of the oligonucleotides. These additional sequences encode sites for the restriction enzymes, EcoRI and SmaI in order to assist in the subsequent cloning of PCR amplified DNA into appropriate vectors. An oligo (dT) primer which also contained EcoRI and SmaI restriction sites was synthesised for use in the PCR.

```
A140/301  (SEQ ID NO:8)   GCGAATTCCCGGG.GCG.AAA.AAA.AAT.TAT.GAA.AC
                                       A   G   G   C   C   G
                                       T
                                       C

A140/302  (SEQ ID NO:9)   GCGAATTCCCGGG.GAG.CCG.CCG.CCG.GGT.GAA.TTG.CA
                                       A   A   A   A   C   G   A
                                                           T   T   T       T
                                                           C   C   C       C

A140/303  (SEQ ID NO:10)  GCGAATTCCCGGG.CAA.ATT.ATT.GGG.ACG.ACG.ATG
                                       G   C   C   A   A   A
                                               A   A   T   T   T
                                                           C   C   C
```

(b) RNA isolation and cDNA library construction.

Total RNA was isolated from 1 g (wet weight) of *H. contortus* using an RNA extraction kit purchased from Pharmacia (Cat #XY-016-00-01). Nematodes were recovered from the abomasum of sheep 15 days after infestation with exsheathed L3 stage parasites and stored at −70° C. after snap freezing in liquid nitrogen. In order to extract RNA, the frozen worms were pulverized under liquid nitrogen, added to 7 ml of extraction solution (which is a buffered aqueous solution containing guanidine thiocyanate, N-lauryl sarcosine and EDTA; density at 25° C.=1.15 g/ml) and then layered over 2×1.25 ml cushions of CsTFA (buffered aqueous solution containing CsTFA; density at 25° C.=1.51 g/ml) in 13×51 mm polyallomer tubes. The gradients were centrifuged at 31,000 rpm for 16 hours at 15° C. using an SW 50.1 rotor in an L8-70 Beckman ultracentrifuge. After centrifugation, pellets of RNA were dissolved in TE buffer (10 mM Tris-HCl, pH 7.5, 1 mM EDTA) and reprecipitated from ethanol at −20° C. The sedimented RNA was then dissolved again in TE and further purified by centrifugation through an oligo (dT)-cellulose column (Pharmacia mRNA Purification Kit, Cat #XY-012-00-02) as described by the manufacturer. The resulting purified poly (A)⁺RNA was used to construct a cDNA library.

cDNA libraries were prepared using a Pharmacia cDNA Synthesis Kit (Cat #XY-003-00-03). Briefly, polyadenylated RNA purified from 325 mg total RNA was used as a template for oligo (dT) primed cDNA synthesis using Moloney Murine Leukemia Virus Reverse Transcriptase. Second strand cDNA synthesis was accomplished using RNase H and *E coli* DNA polymerase I. The double stranded cDNA was then treated with the Klenow fragment of DNA polymerase and ligated to EcoRI/NotI adaptors. The cDNA was then incubated with T4 polynucleotide kinase and ligated into EcoRI digested, dephosphorylated lambda gt 10 arms and packaged in vitro into infectious bacteriophage particles. The lambda gt 10 arms and packaging mixes were obtained from Promega (Protoclone lambda gt 10 System and Pacagene System). Methods used were as directed by the supplier. The packaged cDNA was transfected into *E. coli* C600 Hfl and plated on Luria agar plates using Luria top agar containing 10 mM MgSO₄. A total of 6×10⁷ plaque forming units were obtained of which 98% were recombinants with an average insert size of 2.0 kbp.

(c) Preparation of probes for screening

A 40 kD antigen-specific double stranded DNA probe was prepared using PCR. The procedure used was based on that described by Saiki et al (1988) and used a cloned form of Taq polymerase obtained from Perkin Elmer Cetus. Two milligrams total RNA was annealed to 100 ng oligo (dT) PCR primer in 6 µl water by heating to 70° C. for 5 minutes and then leaving to cool to room temperature. The annealed RNA-oligo (dT) was then incubated with 200 units of reverse transcriptase (BRL) in the presence of 50 mM Tris-HCl (pH 8.3), 75 mM KCl, 10 mM MgCl₂, 5 mM spermidine, 10 mM DTT, 1 unit RNasin for 1 hour at 37° C. in a final volume of 25 µl. A similar reaction from which reverse transcriptase was omitted was also carried out to be used subsequently as a negative control for the PCR.

The PCR was performed on cDNA produced as described above. The reaction mixture contained first strand cDNA synthesized from 1 mg total RNA, 1 µM each of one of A140/301, A140/302 or A140/303 (SEQ ID NOS. 8, 9 and 10, respectively) and 1 µM oligo (dT) PCR primer, 200 µM of each DNTP, 50 mM KCl, 10 mM Tris-HCl (pH 9.0), 2 mM MgCl₂, 0.01% gelatin, 0.01% Triton X-100 and 2 units of Taq polymerase in a total volume of 100 µl. Amplification took place over 25 cycles, each of which consists of denaturation for 1 minute at 94° C., annealing for 2 minutes at 40° C. and extension for 3 minutes at 72° C.

Samples of each PCR reaction were analysed on a 0.8% agarose gel at the end of the reactions. In the reaction containing primer A140/303 (SEQ ID NO:10) and oligo (dT), a unique band of approximately 700 bp was seen. Several other bands were present but these were also seen in the reaction in which oligo (dT) only was used. The approximately 700 bp band was not seen when primers A140/301 (SEQ ID NO:8) or A140/302 (SEQ ID NO:9) were used. No bands were seen in the reverse transcriptase negative control.

The specific 700 bp PCR product was digested with EcoRI, purified on an agarose gel, ligated into pUC19 using conventional techniques (Maniatis et al, 1982) and sequenced using the dideoxy chain termination procedure (Amersham Microtitre Plate Sequencing Kit, Cat #RPN.1590). Sequence analysis of the ends of the clone confirmed that it contained the sequence of primer A140/303 (SEQ ID NO:10) at the 5' end and a poly (A) stretch at the 3' end. Translation of the DNA sequence further into the clone from the 5' end indicated homology with the amino terminal sequence of the mature protein (SEQ ID NO:7) obtained previously and described in Example 5. Since the sequence of this clone confirmed that it contained sequence encoding the 40 kD antigen, DNA was isolated, digested with EcoRI and the insert was purified and used to hybridise to the CDNA library described in (b).

Approximately 10⁵ plaque forming units were screened by hybridization of nitrocellulose filter replicas of the library in a solution containing 2×10⁵ cpm/ml probe, 5× SSPE, 5× Denhardt's solution, 0.5% (w/v) SDS, 20 µg/ml sheared, denatured salmon sperm DNA at 55° C. After washing the filters at 60° C. in 0.5× SSC, 0.1% SDS, and autoradiography, 23 positive plaques were identified. Of these, 19 were picked for subsequent purification and analysis. Not I inserts were isolated from the purified phage DNA and subcloned into PGEM 5zf(+) (Promega) for further analysis. The sequence of one of these clones (pBTA983) is shown in FIG. 1 and in SEQ ID NO:12. There is one continuous open reading frame of 657 nucleotides followed by a translation stop codon, TAA.

The open reading frame does not have a methionine initiation codon at the 5' end of the clone so this clone does not represent the complete coding region. However, it can be seen clearly that the amino terminal sequence predicted from the nucleotide sequence is homologous to the amino acid sequence obtained from purified culture fluid antigen (SEQ ID NO:7). In addition, the amino acids N-terminal to this sequence are hydrophobic which is characteristic of leader sequences and there is a potential cleavage recognition site for signal peptidase which processes such leader sequences. It is therefore likely that the cDNA clone codes for the majority of the antigen.

The DNA sequence for several other cDNA clones has also been determined and it is clear that there is family of related genes. The amino terminal sequences predicted from other cDNA clones isolated from the same cDNA library diverge from the sequence obtained from the native protein (SEQ ID NO:7) and from the cDNA sequence of clone pBTA 983 (SEQ ID NO:13). The majority of the rest of the DNA sequence is conserved among these clones, varying by about 20% at the amino acid level. It appears that the N-terminus of this antigen is hypervariable and that the cDNA molecules belong to a gene family. This is further supported by the Southern blot. Lane 2 shows the hybridisation pattern obtained with *H contortus* DNA probed with the NotI fragment from pBTA983. As well as a band hybridising strongly at about 1070 bp, there are several other bands hybridising at lower intensity indicating the presence of many related genes.

Example 7

Expression of the 40 kD Antigen in *E.coli*

A number of systems could be used to express the recombinant 40 kD antigen, e.g. mammalian cells, baculovirus infected insect cells, yeasts, or bacteria. As an example, the gene was expressed in *E.coli*. The cDNA fragment from pBTA 983 was isolated (without the segment coding for the hydrophobic signal sequence) as a 700 bp Bam HI/Sal I fragment, and was subcloned into *E.coli* expression vector pBTA721. When expression was induced by heat-shock at 42° C., a fusion protein with 14 N-terminal amino acids encoded by the vector, fused to the 40 kD protein was produced. The apparent molecular weight of the fusion protein was approximately 29 kD as expected as it is not glycosylated by *E.coli*. The fusion protein reacted with rabbit serum raised against culture fluid in Western blots.

Such a fusion protein could be purified from the bacterial cells by standard methods known in the art and, possibly following a refolding step in the presence of reagents such as reduced and oxidised glutathione (which facilitate sulphydryl bond interchange), the recombinant antigen could be formulated into a suitable adjuvant and used to stimulate a protective immune response in target animals such as sheep.

Example 8

Expression of *H. contortus* 40 kD Antigen in Insect Cells

The baculovirus expression system enables eukaryotic proteins to be produced in insect cells in a near-native conformation (Luckow and Summers, 1988). Purification of such proteins is often facilitated if they are secreted into the culture supernatant. We describe here one means by which the cDNA clone encoding the 40 kD antigen can be manipulated in a way that enables the production of 40 kD antigen and its secretion into the culture supernatant of insect cells infected with the recombinant baculovirus.

An oligonucleotide (5'-CAAAT GGATCC TATAAAT ATG CGT GGC ATC GCT TTG TTC GTA CTA ACG ATT CTG-3' SEQ ID NO:11 ) was made with the following features; a Bam H1 restriction site, the 7 nucleotides found immediately upstream of the initiating methionine of the polyhedrin gene from the baculovirus ACMNPV (Summers and Smith, 1987), the 18 nucleotides encoding the first six hydrophobic amino acids of the leader sequence from the Bm86 gene from the tick *Boophilus microplus* (Rand et al. 1989) and the 18 nucleotides encoding the first six amino acids of the cDNA clone for pBTA983 (FIG. 1).

In conjunction with a commercially available primer (Sp6, Promega) the oligonucleotide was used in a PCR reaction to generate DNA molecules encoding 40 kD antigen containing a hybrid Bm86/40 kD secretion signal. The plasmid used for the PCR reaction has the 40 kD cDNA fragment inserted at the Not1 site of pGEMSZf (+) (Promega), with the 5' end of the 40 kD coding strand adjacent to the T7 promoter.

The PCR products were digested with Bam H1, and Eco R1 (cuts at position 83 in the 40 kD coding region, see FIG. 1). The 104 bp fragment was purified from a low melting agarose gel and subcloned into pSp72 (Promega) cut with Bam HI and Pst 1 in a three way ligation with the 695 bp Eco R1/Pst 1 fragment encoding 40 kD antigen from nucleotide position 83 on. After transformation of a suitable *E.coli* host, plasmid DNA from several clones was isolated and screened by sequencing for any errors introduced during PCR amplification. A clone with the correct sequence was chosen, the Bam H1/Pst 1 fragment encoding 40 kD antigen with the hybrid Bm86/40 kD secretion signal was isolated and subcloned into a baculovirus transfer vector (Lucknow and Summers, 1988).

A recombinant baculovirus was plaque purified using a combination of plaque hybrization and visual screening techniques and used to infect insect cells (Summers and Smith, 1987). The 40 kD antigen was purified from the culture supernatant.

EXAMPLE 9

Purification of Recombinant 40kD Expressed by Baculovirus/Sf 9 Cells

Culture medium of Sf9 cells containing secreted 40 kD antigen was concentrated ten-fold using a Amicon SIY30 spiral cartridge. The retentate was incubated with lentil lectin-Sepharose 4B overnight at 4° C. Bound material was specifically eluted with 0.2 M methyl-D-mannoside. The non-bound material was recycled through the column and the combined bound fractions were concentrated two-fold and subjected to gel filtration on a Sephacryl S-300 HR column. The fraction containing the secreted 40 kD antigen was dialysed and passed over a Q-Sepharose fast flow column which was resolved with a linear 0–0.3M NaCl gradient. The purified 40 kD was judged to be at least 90% pure by SDS-PAGE and Coomassie Blue R-250 staining.

EXAMPLE 10

Vaccination of Guinea Pigs with Purified Recombinant 40 kD

The recombinant 40 kD antigen purified from Baculovirus/Sf9 culture medium was used to vaccinate guinea pigs as described in Example 2. it can be seen (Table 4) that the recombinant 40 kD antigen gave significant protection when injected with amounts similar to those used in the experiments with the native 40 kD antigen (Example 4).

| Expt No. | Group | Injected (μg) | n | Worm Nos. | Protection (%) |
|---|---|---|---|---|---|
| 357 | Controls | — | 12 | 701 ± 208 | — |
|  | Vaccinates | 40 | 8 | 385 ± 192 | 45 |

Vaccinates were injected intraperitoneally with the antigen. Animals were challenged 28 days later and killed for worm counts 5 days post challenge.

EXAMPLE 11

Homologous Genes Related to that of the Protective Antigen are Present in Other Species of Parasitic Nematode DNA hybridisation (or Southern bolt analysis) was carried out using standard techniques (Maniatis et al., 1982) to determine whether other species of parasitic nematodes have genes which are "homologous" to that coding for the *H contortus* protective antigen (FIG. 3). The Eco RI insert of the cDNA clone pBTA983 described in Example 6 was used as a hybridisation probe to DNA isolated from a number of other species of parasitic nematodes. As well as hybridizing strongly to several restriction fragments in the DNA isolated from the homologous species, i.e., *H. contortus*, as expected, the probe also hybridized to specific restriction fragments in DNA isolated from *Dirofilaria immitis* and *Trichostrongylus colubriformis*. The blots were washed at a stringency that suggested that the level of homology was at least 50%.

This clearly demonstrates that there are genes which are closely related to that coding for the protective antigen in these other species of parasitic nematodes and by extension, in all species of parasitic nematodes. These genes could be isolated using standard molecular biological techniques, and recombinant organisms could be made which synthesise those related or homologous antigens from the other species of parasitic nematode. The present inventors consider that the related antigens will serve as effective immunogens to provide protection to vaccinated animals against infection by the other species of parasite. In addition, related antigens isolated from a broad range of parasitic nematodes could be isolated and provide effective protective immunogens to protect animals against infestation by an extensive range of such nematodes.

It has already been demonstrated that this approach can be successful (International Application No. PCT/AU88/00239). That patent application describes how an antigen was purified from a homogenate of *T. colubriformis* based on the ability of that antigen to provide protection to guinea pigs against challenge infections by *T. colubriformis*. Amino acid sequence information was determined for this antigen which enabled the gene coding for the antigen to be isolated from recombinant DNA libraries. The DNA coding for the *T. colubriformis* gene was then used as a hybridisation probe to identify recombinant organisms coding for the "homologous" antigen from *H. contortus*. Recombinant organisms were then constructed which synthesised the *H. contortus* antigen which was then used in vaccination and challenge trials in sheep and guinea pigs. The *H. contortus* recombinant antigen provided protection to vaccinated sheep against infestation by *H. contortus* and provided protection to guinea pigs against challenge infection by *T. colubriformis*.

This demonstrates that it is possible, given the DNA sequence homology demonstrated in the above hybridisation experiments, to use the cloned DNA sequence coding for protective antigen from one species of parasitic nematode to identify clones coding for the homologous gene products from other species of parasitic nematodes, engineer those recombinant organisms to express the homologous antigen and use this in a vaccine to provide protection against the other species of parasitic nematode. It is considered that a natural extension of the results presented here is to do so with the DNA sequence of the present invention.

It is to be understood that the nucleotide sequence of the homologous genes and the amino acid sequence of the homologous antigens may not be identical to those of the first target species but will be related by at least 50% over a stretch of at least 60 base pairs and preferably the relationship would be 70% or more over this same region with the relationship at the amino acid level being at least 70% over 20 amino acids. In most cases, this degree of homology would be sufficient to enable an unambiguous identification of the relatedness of the two genes or proteins.

EXAMPLE 12

Immunological Cross-Reactivity between Antibodies to the 40 kD Antigen and *Dirofilaria Immitis* Proteins Antiserum from sheep vaccinated with the 40 kD antigen was used to probe a Western blot of extracts (pre-enriched by binding and specific elution from lentil lectin-Sepharose 4B) from adult *D. immitis* and infective *H. contortus* larvae. After development with a second antibody conjugated to horse radish-peroxidase two antigens from each species were shown to be reactive. A major band of 40 kD was detected in both with a minor band in the 55–68 kD range. Antigens of very similar molecular weight were also detected in culture fluid run on the same Western blot.

This result supports other observations (Example 11) using DNA hybridization techniques, that genes related to the 40 kD antigen genes are present, and expressed in, *D. immitis*.

EXAMPLE 13

Scale up of Manufacturing for Commercial Vaccines

The production and purification techniques so far described are carried out at laboratory scale. For commercial production of the antigens of the invention, large scale fermentation of transformed hosts is required.

The large scale fermentations are performed according to standard techniques, the particular techniques selected being appropriate to the transformed host used for production of the antigen.

Deposition of Microorganisms

Strain BTA 2147, which is *E. coli* JM109 containing the plasmid PBTA 983, has been deposited with Australian Government Analytical Laboratories of 1 Suakin Street, Pymble 2073, New South Wales, Australia in accordance with the provisions of the Budapest Treaty on 29 Jan. 1992 under accession number N92/4389.

The genotype of *E. coli* JM109 is BTA2147 is: JM109 strain, genotype: endA1, recA1, gyrA96, thi, hsdR17(rk_, mk$_+$), relA1, supE44, $\lambda_-$, $\Delta$(lac-proAB), [F', traD36, proAB, lacI$_q$Z$\Delta$M15].

pBTA 983 is pGEM5Zf(+)m (Promega, Madison, Wis., USA), containing a 776 base pair NotI insertion coding for a portion of an antigenic protein from the gasto-intestinal nematode, *Haemonchus contortus*.

INDUSTRIAL APPLICATION

The present invention has utility in the field of providing vaccines for protection of mammalian hosts against infestation by parasitic nematodes.

REFERENCES

Maniatis T, Fritsch E F and Sambroook J (eds) (1982) Molecular Cloning: A Laboratory Manual, CSH Laboratory, Cold Spring Harbor.

O'Donnell I J, Dineen J R, Rothwell T L W and Marshall R C (1985) "Attempts to probe the antigens and protective immunogens of *Trichostrongylus colubriformis* in immunoblots with sera from infected and hyperimmune sheep and high and low responder guinea pigs". *Int. J. Parasitol.* 15, 129–136.

Saiki R K, Gelfand D H, Stoffel S, Scharf S J, Higuchi R, Horn G T, Mullis K B, and Erlich H A (1988) Primer-directed enzymatic amplification of DNA with a thermostable DNA polymerase. *Science* 239, 487–491.

Scher M G, Resneck W G and Bloch R J (1989) *Analytical Biochemistry* 177, 168–171.

Summers M D, Smith G E. (1987) Texas Agricultural Experimental Station Bulletin No. 1555.

Lucknow V A and Summers M D (1988) *Biotechnology* 6, 47–55.

Rand K N, Moore T, Sriskantha A et al. (1989) *Proc. Natl. Acad. Sci. USA*. 86, 9657–9611.

We claim:

1. An isolated polynucleotide molecule comprising a sequence encoding a polypeptide comprising amino acid residues 13–219 of SEQ ID NO: 13.

2. An isolated polynucleotide molecule according to claim 1, wherein said polynucleotide molecule is a DNA molecule.

3. A polynucleotide molecule according to claim 2 wherein the polynucleotide molecule is a cDNA molecule.

4. An isolated polynucleotide molecule according to claim 2, comprising nucleotides 44 to 664 of SEQ ID NO: 12.

5. An isolated polynucleotide molecule according to claim 2, comprising nucleotides 8 to 667 of SEQ ID NO: 12.

6. An isolated polynucleotide molecule according to claim 2, comprising the nucleotide sequence of SEQ ID NO: 12.

7. An isolated polynucleotide molecule according to claim 2, further comprising vector DNA.

8. An isolated polynucleotide molecule according to claim 7, wherein said vector DNA is selected from the group consisting of plasmid, viral and cosmid DNA.

9. An isolated polynucleotide molecule according to claim 8, wherein said vector DNA is selected from the group consisting of pGEM5Zf(+), pBTA721, lambda gt11, pUR290, pUR291, pUR292, pUK270, pUC8, pUC9, pZipNeo, an SV40 based vector, lambda gt10, an EMBL vector, pBR327, pBR329, pBR329 containing a par locus, baculovirus and vaccinia virus.

10. A transformed host cell, wherein said host cell is transformed with an isolated DNA molecule according to claim 2.

11. A transformed host cell according to claim 10, wherein said host cell is selected from the group consisting of bacterial, yeast, fungi other than yeast, insect, plant and mammalian cells.

12. A transformed host cell according to claim 11, wherein said host cell is *E. coli*.

13. Plasmid pBTA983.

14. *E. coli* strain BTA 2147 (AGAL Accession No. N24389).

15. A process for preparing a recombinant DNA molecule according to claim 7, comprising inserting an isolated polynucleotide molecule encoding a polypeptide comprising amino acid residues 13–219 of SEQ ID NO: 12 into a DNA vector.

16. A process for preparing a transformed host cell, comprising transforming a host cell with a recombinant DNA molecule according to claim 7.

17. A whole cell vaccine, comprising a transformed host according to claim 10 together with a pharmaceutically and/or veterinarally acceptable carrier, diluent, excipient and/or adjuvant.

18. A whole cell vaccine, comprising a transformed host according to claim 10 together with a pharmaceutically and/or veterinarally acceptable carrier, diluent, excipient and/or adjuvant.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Haemonchus contortus ( x i ) SEQUENCE DESCRIPTION: SEQ ID NO:1:

Lys Gln Pro Asn Thr Pro Leu Gly Pro Lys
 1               5                  10

( 2 ) INFORMATION FOR SEQ ID NO:2:

( i ) SEQUENCE CHARACTERISTICS:
    ( A ) LENGTH: 22 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Haemonchus contortus ( i x ) FEATURE:
    ( A ) NAME/KEY: Modified-site
    ( B ) LOCATION: 2
    ( D ) OTHER INFORMATION: /note= "May be Leu or Val"

( i x ) FEATURE:
    ( A ) NAME/KEY: Modified-site
    ( B ) LOCATION: 15
    ( D ) OTHER INFORMATION: /note= "Amino acid unknown"

( i x ) FEATURE:
    ( A ) NAME/KEY: Modified-site
    ( B ) LOCATION: 19
    ( D ) OTHER INFORMATION: /note= "Amino acid unknown"

( x i ) SEQUENCE DESCRIPTION: SEQ ID NO:2:

Lys Xaa Ser Leu Met Gly Asn Ala Tyr Arg Thr Leu Ala Asp Xaa Gly
 1               5                  10                  15

Val Phe Xaa Tyr Pro Pro
            20

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Haemonchus contortus ( i x ) FEATURE:
    ( A ) NAME/KEY: Modified-site
    ( B ) LOCATION: 3
    ( D ) OTHER INFORMATION: /note= "Amino acid unknown"

( i x ) FEATURE:

-continued (A) NAME/KEY: Modified-site
                (B) LOCATION: 11
                (D) OTHER INFORMATION: /note= "Amino acid unknown"

(ix) FEATURE:
                (A) NAME/KEY: Modified-site
                (B) LOCATION: 14
                (D) OTHER INFORMATION: /note= "Amino acid unknown"

(ix) FEATURE:
                (A) NAME/KEY: Modified-site
                (B) LOCATION: 15
                (D) OTHER INFORMATION: /note= "Amino acid unknown"

(ix) FEATURE:
                (A) NAME/KEY: Modified-site
                (B) LOCATION: 19
                (D) OTHER INFORMATION: /note= "May be Gly or Leu"

(xi) SEQUENCE DESCRIPTION: SEQ ID NO:3:

Lys  Asn  Xaa  Glu  Thr  Ser  Glu  Pro  Pro  Xaa  Glu  Phe  Xaa  Xaa  Gln
    1                  5                        10                       15

Ile  Ile  Xaa  Gly
                    20

(2) INFORMATION FOR SEQ ID NO:4:

(i) SEQUENCE CHARACTERISTICS:
                (A) LENGTH: 14 amino acids
                (B) TYPE: amino acid
                (D) TOPOLOGY: linear (ii) MOLECULE TYPE: peptide (vi) ORIGINAL SOURCE:
                (A) ORGANISM: Haemonchus contortus (ix) FEATURE:
                (A) NAME/KEY: Modified-site
                (B) LOCATION: 2
                (D) OTHER INFORMATION: /note= "Amino acid unknown"

(ix) FEATURE:
                (A) NAME/KEY: Modified-site
                (B) LOCATION: 3
                (D) OTHER INFORMATION: /note= "Amino acid unknown"

(ix) FEATURE:
                (A) NAME/KEY: Modified-site
                (B) LOCATION: 7
                (D) OTHER INFORMATION: /note= "May be Ser or Pro"

(ix) FEATURE:
                (A) NAME/KEY: Modified-site
                (B) LOCATION: 11
                (D) OTHER INFORMATION: /note= "May be Glu or Asp"

(ix) FEATURE:
                (A) NAME/KEY: Modified-site
                (B) LOCATION: 12
                (D) OTHER INFORMATION: /note= "Amino acid unknown"

(xi) SEQUENCE DESCRIPTION: SEQ ID NO:4:

Lys  Xaa  Xaa  Glu  Thr  Ser  Xaa  Pro  Pro  Pro  Xaa  Xaa  Phe  Phe
    1                  5                        10

(2) INFORMATION FOR SEQ ID NO:5:

(i) SEQUENCE CHARACTERISTICS:
                (A) LENGTH: 19 amino acids
                (B) TYPE: amino acid
                (D) TOPOLOGY: linear (ii) MOLECULE TYPE: peptide (vi) ORIGINAL SOURCE:
   (A) ORGANISM: Haemonchus contortus (ix) FEATURE:
   (A) NAME/KEY: Modified-site
   (B) LOCATION: 3
   (D) OTHER INFORMATION: /note= "Amino acid unknown"

(ix) FEATURE:
   (A) NAME/KEY: Modified-site
   (B) LOCATION: 14
   (D) OTHER INFORMATION: /note= "Amino acid unknown"

(ix) FEATURE:
   (A) NAME/KEY: Modified-site
   (B) LOCATION: 18
   (D) OTHER INFORMATION: /note= "Amino acid unknown"

(xi) SEQUENCE DESCRIPTION: SEQ ID NO:5:

Lys Asn Xaa Glu Thr Ser Glu Pro Pro Asp Glu Phe Xaa Gly Gln
1               5                   10                  15

Ile Xaa Gly (2) INFORMATION FOR SEQ ID NO:6:

(i) SEQUENCE CHARACTERISTICS:
      (A) LENGTH: 14 amino acids
      (B) TYPE: amino acid
      (D) TOPOLOGY: linear (ii) MOLECULE TYPE: peptide (vi) ORIGINAL SOURCE:
      (A) ORGANISM: Haemonchus contortus (ix) FEATURE:
      (A) NAME/KEY: Modified-site
      (B) LOCATION: 9
      (D) OTHER INFORMATION: /note= "May be Gln or Tyr"

(ix) FEATURE:
      (A) NAME/KEY: Modified-site
      (B) LOCATION: 14
      (D) OTHER INFORMATION: /note= "May be Gly or Ser"

(xi) SEQUENCE DESCRIPTION: SEQ ID NO:6:

Lys Tyr Ala Met Val Leu Gly Asn Xaa Gln Ala Pro Leu Xaa
1               5                   10

(2) INFORMATION FOR SEQ ID NO:7:

(i) SEQUENCE CHARACTERISTICS:
      (A) LENGTH: 38 amino acids
      (B) TYPE: amino acid
      (D) TOPOLOGY: linear (ii) MOLECULE TYPE: protein (v) FRAGMENT TYPE: N-terminal (vi) ORIGINAL SOURCE:
      (A) ORGANISM: Haemonchus contortus (ix) FEATURE:
      (A) NAME/KEY: Modified-site
      (B) LOCATION: 1
      (D) OTHER INFORMATION: /note= "May be Ala or Asp"

(ix) FEATURE:
      (A) NAME/KEY: Modified-site
      (B) LOCATION: 2
      (D) OTHER INFORMATION: /note= "May be Lys or Thr"

(ix) FEATURE:
      (A) NAME/KEY: Modified-site

```
                ( B ) LOCATION: 3
                ( D ) OTHER INFORMATION: /note= "May be Lys or Glu"

( i x ) FEATURE:
                ( A ) NAME/KEY: Modified-site
                ( B ) LOCATION: 17
                ( D ) OTHER INFORMATION: /note= "Amino acid unknown"

( i x ) FEATURE:
                ( A ) NAME/KEY: Modified-site
                ( B ) LOCATION: 20
                ( D ) OTHER INFORMATION: /note= "Amino acid unknown"

( i x ) FEATURE:
                ( A ) NAME/KEY: Modified-site
                ( B ) LOCATION: 25
                ( D ) OTHER INFORMATION: /note= "Amino acid unknown"

( i x ) FEATURE:
                ( A ) NAME/KEY: Modified-site
                ( B ) LOCATION: 29..30
                ( D ) OTHER INFORMATION: /note= "Amino acids unknown"

( i x ) FEATURE:
                ( A ) NAME/KEY: Modified-site
                ( B ) LOCATION: 32
                ( D ) OTHER INFORMATION: /note= "Amino acid unknown"

( i x ) FEATURE:
                ( A ) NAME/KEY: Modified-site
                ( B ) LOCATION: 34
                ( D ) OTHER INFORMATION: /note= "Amino acid unknown"

( x i ) SEQUENCE DESCRIPTION: SEQ ID NO:7:

Xaa Xaa Xaa Asn Tyr Glu Thr Ser Glu Pro Pro Asp Glu Phe His
 1           5                  10                  15

Xaa Gln Ile Xaa Gly Thr Thr Met Xaa Pro Glu Lys Xaa Xaa Leu Xaa
            20                  25                  30

Val Xaa Leu Gly Asn Ala
        35

( 2 ) INFORMATION FOR SEQ ID NO:8:

( i ) SEQUENCE CHARACTERISTICS:
                ( A ) LENGTH: 33 base pairs
                ( B ) TYPE: nucleic acid
                ( C ) STRANDEDNESS: double
                ( D ) TOPOLOGY: linear ( i x ) FEATURE:
                ( A ) NAME/KEY: modified_base
                ( B ) LOCATION: 16

( i x ) FEATURE:
                ( A ) NAME/KEY: modified_base
                ( B ) LOCATION: 19

( i x ) FEATURE:
                ( A ) NAME/KEY: modified_base
                ( B ) LOCATION: 22

( i x ) FEATURE:
                ( A ) NAME/KEY: modified_base
                ( B ) LOCATION: 25

( i x ) FEATURE:
                ( A ) NAME/KEY: modified_base
                ( B ) LOCATION: 28

( i x ) FEATURE:
                ( A ) NAME/KEY: modified_base
                ( B ) LOCATION: 31

( x i ) SEQUENCE DESCRIPTION: SEQ ID NO:8:

GCGAATTCCC GGGGCNAARA ARAAYTAYGA RAC                                33
```

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i x ) FEATURE:
        ( A ) NAME/KEY: modified_base
        ( B ) LOCATION: 16

( i x ) FEATURE:
        ( A ) NAME/KEY: modified_base
        ( B ) LOCATION: 19

( i x ) FEATURE:
        ( A ) NAME/KEY: modified_base
        ( B ) LOCATION: 22

( i x ) FEATURE:
        ( A ) NAME/KEY: modified_base
        ( B ) LOCATION: 25

( i x ) FEATURE:
        ( A ) NAME/KEY: modified_base
        ( B ) LOCATION: 28

( i x ) FEATURE:
        ( A ) NAME/KEY: modified_base
        ( B ) LOCATION: 31

( i x ) FEATURE:
        ( A ) NAME/KEY: modified_base
        ( B ) LOCATION: 34

( x i ) SEQUENCE DESCRIPTION: SEQ ID NO:9:

GCGAATTCCC GGGGARCCNC CNCCNGGYGA RTTNCA    36

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i x ) FEATURE:
        ( A ) NAME/KEY: modified_base
        ( B ) LOCATION: 16

( i x ) FEATURE:
        ( A ) NAME/KEY: modified_base
        ( B ) LOCATION: 19

( i x ) FEATURE:
        ( A ) NAME/KEY: modified_base
        ( B ) LOCATION: 22

( i x ) FEATURE:
        ( A ) NAME/KEY: modified_base
        ( B ) LOCATION: 25

( i x ) FEATURE:
        ( A ) NAME/KEY: modified_base
        ( B ) LOCATION: 28

( i x ) FEATURE:
        ( A ) NAME/KEY: modified_base
        ( B ) LOCATION: 31

( x i ) SEQUENCE DESCRIPTION: SEQ ID NO:10:

GCGAATTCCC GGGCARATHA THGGNACNAC NATG    34

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:11:

```
CAAATGGATC CTATAAATAT GCGTGGCATC GCTTGTTCG TACTAACGAT TCTG         54
```

(2) INFORMATION FOR SEQ ID NO:12:

(i) SEQUENCE CHARACTERISTICS:
        (A) LENGTH: 776 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: Haemonchus contortus (ix) FEATURE:
        (A) NAME/KEY: CDS
        (B) LOCATION: 8..667

(xi) SEQUENCE DESCRIPTION: SEQ ID NO:12:

```
CGGCCGC TTC GTA CTA ACG ATT CTG GTG GCT TCG GCA TCT TCG GCA ACG         49
        Phe Val Leu Thr Ile Leu Val Ala Ser Ala Ser Ser Ala Thr
         1               5                  10

AAA AAT TGC GAG ACT TCA GAA CCT CCT CCA GAT GAA TTC CAT TGT CAA         97
Lys Asn Cys Glu Thr Ser Glu Pro Pro Pro Asp Glu Phe His Cys Gln
 15              20                  25                  30

ATC AAC GGC ACC ACC ATG ACC CCT GAA AAA CGA AAG CTT TCC GTA ATG        145
Ile Asn Gly Thr Thr Met Thr Pro Glu Lys Arg Lys Leu Ser Val Met
                 35                  40                  45

CTG GGA AAT GCT TAT CGT ACA CTA GCA ACA TCT GGA GTA TTT GGG TAT        193
Leu Gly Asn Ala Tyr Arg Thr Leu Ala Thr Ser Gly Val Phe Gly Tyr
             50                  55                  60

CCA CCA AGC CAG AAC ATG TAT CAA TTG AAC TAC TCC TGC TTG GCT GAG        241
Pro Pro Ser Gln Asn Met Tyr Gln Leu Asn Tyr Ser Cys Leu Ala Glu
         65                  70                  75

AAA TAT GCA ATG GTA CTC TGC AAC CAA CAA GCA CCA CTC AAA CCT GTA        289
Lys Tyr Ala Met Val Leu Cys Asn Gln Gln Ala Pro Leu Lys Pro Val
     80                  85                  90

GGG TAC AAT CTG TCT TCT ATC CCA TTA GCA GCA GCA TTC GAA TTG TGG        337
Gly Tyr Asn Leu Ser Ser Ile Pro Leu Ala Ala Ala Phe Glu Leu Trp
 95                 100                 105                 110

TGG GGC AAT CAC GAC TTT GGT GCT TTT ATC AAT GAA ACT GGA GTC TAC        385
Trp Gly Asn His Asp Phe Gly Ala Phe Ile Asn Glu Thr Gly Val Tyr
                115                 120                 125

AGC CCT AAC TTT GAT TAT ACC GTG TTC ACA CAA ATG GTT TCG GGT TAC        433
Ser Pro Asn Phe Asp Tyr Thr Val Phe Thr Gln Met Val Ser Gly Tyr
            130                 135                 140

GCC GTC AGT ATA GGG TGC ACC GAT ACG TGC TAT GGC AAA CAA CAG GCG        481
Ala Val Ser Ile Gly Cys Thr Asp Thr Cys Tyr Gly Lys Gln Gln Ala
        145                 150                 155

TAT TGC GCA TTC GAA GTT TGC ACA GCC ATG ACT TAC TTC GGC ATG ATC        529
Tyr Cys Ala Phe Glu Val Cys Thr Ala Met Thr Tyr Phe Gly Met Ile
    160                 165                 170

TAC GAA GCA GGA TCT GGT CCA TGT ATG GCC GAT AGT GAC TGC ACC ACG        577
Tyr Glu Ala Gly Ser Gly Pro Cys Met Ala Asp Ser Asp Cys Thr Thr
175                 180                 185                 190
```

-continued

```
TAT  CCT  GGG  TCC  ACG  TGC  AAT  ATG  GCA  AAT  GGA  TTG  TGT  GTC  AAG  CAA         625
Tyr  Pro  Gly  Ser  Thr  Cys  Asn  Met  Ala  Asn  Gly  Leu  Cys  Val  Lys  Gln
               195                      200                      205

CCA  AAC  ACT  CCT  CTC  TGC  CCG  AAA  AAG  ACA  AAC  TTA  TAT  TAACGGCAAC             674
Pro  Asn  Thr  Pro  Leu  Cys  Pro  Lys  Lys  Thr  Asn  Leu  Tyr
               210                      215                 220

AACAATAACA  ATAATCCCAT  CCCATATACA  GCCTTACAAC  TCCGTCTAAT  GCTGATAATC                  734

ACATATTAAT  TACAATGGGA  AGGAGAATAA  ATTGCGGCCG  CC                                      776
```

( 2 ) INFORMATION FOR SEQ ID NO:13:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Phe  Val  Leu  Thr  Ile  Leu  Val  Ala  Ser  Ala  Ser  Ser  Ala  Thr  Lys  Asn
 1                   5                    10                       15

Cys  Glu  Thr  Ser  Glu  Pro  Pro  Asp  Glu  Phe  His  Cys  Gln  Ile  Asn
               20                    25                       30

Gly  Thr  Thr  Met  Thr  Pro  Glu  Lys  Arg  Lys  Leu  Ser  Val  Met  Leu  Gly
               35                    40                       45

Asn  Ala  Tyr  Arg  Thr  Leu  Ala  Thr  Ser  Gly  Val  Phe  Gly  Tyr  Pro  Pro
          50                    55                       60

Ser  Gln  Asn  Met  Tyr  Gln  Leu  Asn  Tyr  Ser  Cys  Leu  Ala  Glu  Lys  Tyr
 65                   70                    75                            80

Ala  Met  Val  Leu  Cys  Asn  Gln  Gln  Ala  Pro  Leu  Lys  Pro  Val  Gly  Tyr
               85                    90                            95

Asn  Leu  Ser  Ser  Ile  Pro  Leu  Ala  Ala  Ala  Phe  Glu  Leu  Trp  Trp  Gly
              100                   105                  110

Asn  His  Asp  Phe  Gly  Ala  Phe  Ile  Asn  Glu  Thr  Gly  Val  Tyr  Ser  Pro
         115                    120                  125

Asn  Phe  Asp  Tyr  Thr  Val  Phe  Thr  Gln  Met  Val  Ser  Gly  Tyr  Ala  Val
         130                   135                   140

Ser  Ile  Gly  Cys  Thr  Asp  Thr  Cys  Tyr  Gly  Lys  Gln  Gln  Ala  Tyr  Cys
145                        150                   155                       160

Ala  Phe  Glu  Val  Cys  Thr  Ala  Met  Thr  Tyr  Phe  Gly  Met  Ile  Tyr  Glu
               165                        170                       175

Ala  Gly  Ser  Gly  Pro  Cys  Met  Ala  Asp  Ser  Asp  Cys  Thr  Thr  Tyr  Pro
               180                   185                   190

Gly  Ser  Thr  Cys  Asn  Met  Ala  Asn  Gly  Leu  Cys  Val  Lys  Gln  Pro  Asn
               195                   200                   205

Thr  Pro  Leu  Cys  Pro  Lys  Lys  Thr  Asn  Leu  Tyr
      210                   215
```